United States Patent
Wang et al.

(10) Patent No.: US 10,791,719 B2
(45) Date of Patent: ***Oct. 6, 2020

(54) PERUVIAN SCALLOP×BAY SCALLOP SOUTHERN SUBSPECIES HYBRID THREE-LINE BREEDING SYSTEM AND METHOD

(71) Applicants: Chunde Wang, Shandong (CN); Kuifu Sun, Shandong (CN); Bin Ma, Shandong (CN)

(72) Inventors: Chunde Wang, Shandong (CN); Kuifu Sun, Shandong (CN); Bin Ma, Shandong (CN)

(73) Assignees: QINGDAO AGRICULTURAL UNIVERSITY, Qingdao (CN); QINGDAO OCEANWIDE BIOTECH CO., LTD., Qingdao (CN)

( * ) Notice: Subject to any disclaimer, the term of this patent is extended or adjusted under 35 U.S.C. 154(b) by 317 days.

This patent is subject to a terminal disclaimer.

(21) Appl. No.: 15/320,585

(22) PCT Filed: Sep. 2, 2014

(86) PCT No.: PCT/CN2014/085722
§ 371 (c)(1),
(2) Date: Dec. 20, 2016

(87) PCT Pub. No.: WO2016/029493
PCT Pub. Date: Mar. 3, 2016

(65) Prior Publication Data
US 2017/0196205 A1    Jul. 13, 2017

(30) Foreign Application Priority Data
Aug. 27, 2014 (CN) .......................... 2014 1 0432030

(51) Int. Cl.
*A01K 67/027* (2006.01)
*A01K 61/54* (2017.01)
*A01K 67/033* (2006.01)

(52) U.S. Cl.
CPC ............ *A01K 61/54* (2017.01); *A01K 67/033* (2013.01); *Y02A 40/81* (2018.01)

(58) Field of Classification Search
CPC ...... A01K 67/00; A01K 61/54; A01K 67/033; Y02A 40/81
USPC .......................................................... 800/20
See application file for complete search history.

(56) References Cited

FOREIGN PATENT DOCUMENTS

| CN | 102217561 A | 10/2011 |
|---|---|---|
| CN | 102308770 A | 1/2012 |
| CN | 102318571 A | 1/2012 |

OTHER PUBLICATIONS

ISR for PCT/CN2014/085722 completed Apr. 7, 2015.

*Primary Examiner* — Valarie E Bertoglio
(74) *Attorney, Agent, or Firm* — Guosheng Wang; United States Research and Patent Firm

(57) ABSTRACT

The current invent relates to the construction and application of a three-line breeding system in the Peruvian scallop×bay scallop southern subspecies hybrids. The said three-line consists of a male sterile line, a maintainer line and a restorer line. A combination of male sterile line and maintainer line is obtained by continuously backcrossing the male sterile individuals selected from $F_1$ inter-specific hybrid families with sperm of the selfing family of the sperm-providing bay scallops until the progenies are all male sterile. The restorer line is obtained by continuously backcrossing selected individuals from the male sterile line with sperm of the selfing family of a bay scallop until the progenies are all hermaphroditic and exhibit excellent production traits. Commercial male sterile brood stocks are produced by backcrossing the male sterile line with the maintainer line and commercial hybrid spats are produced by backcrossing the male sterile line and the restorer line.

2 Claims, No Drawings

PERUVIAN SCALLOP×BAY SCALLOP SOUTHERN SUBSPECIES HYBRID THREE-LINE BREEDING SYSTEM AND METHOD

FIELD OF THE INVENTION

The present invention relates to a breeding method for commercial production of hybrid scallops, and in particular, relates to the construction and application of a three-line breeding system, comprising of a male sterile line, a maintainer line and a restorer line, in the Peruvian scallop×bay scallop southern subspecies hybrids.

BACKGROUND OF THE INVENTION

The bay scallop southern subspecies (*Argopecten irradians concentricus*) is native to the U.S. Atlantic coasts. It grows fast and is adapt to a wide range of high temperature with high tolerance to environmental stresses, and is thus very suitable for aquaculture in southern China seas. The bay scallop southern subspecies was first introduced into China in 1991 and now accounts for more than 50% of the total production of cultured scallops in southern China. However, due to long-tem inbreeding after its original introduction, the genetic quality of the Peruvian scallops has heavily degraded, as manifested by its ever-decreasing body size and relatively high mortality rates. Hence, the scallop aquaculture industry has an urgent need for scallop stocks with improved performance especially in growth and survival.

To find a better scallop stock for the sustainable scallop culture industry in China, the inventors introduced the Peruvian scallops (*Argopecten purpuratus*) into China from Peru for the first time in 2007. The Peruvian scallops, which belong to the same genus *Argopecten* as the bay scallop southern subspecies, are fast-growing, medium-sized scallops native to the South Pacific coasts. The two species of *Argopecten* scallops are similar in that both are hermaphroditic scallops with same chromosome number and similar karyotypes, and are thus possible to hybridize with each other. Unlike the bay scallop southern subspecies, culture of the Peruvian scallops in China was not successful as they could not survive the high temperature in the summer or low temperature in the winter. To utilize the genetic resources of the two *Argopecten* scallops, the inventors carried out the interspecific hybridization between the bay scallop southern subspecies and the Peruvian scallops and produced the $F_1$ Peruvian scallop×bay scallop southern subspecies hybrids with superior performance especially in growth. The $F_1$ hybrids exhibited extraordinary high heterosis in growth in that their whole body weight was increased by 72.3% in the *A. purpuratus*×*A. i. concentricus* cohort, compared with that of the bay scallop southern subspecies in the first year (Nan et al., 2012; Wang et al., unpublished).

Despite their high hybrid vigor, the Peruvian scallop×bay scallop southern subspecies hybrids are hard to produce at large scales as both parent stocks are hermaphrodites which release sperm and eggs simultaneously during spawning. The released eggs are prone to being fertilized by sperm of the same scallop or from other animals of the same species, making it hard to collect unfertilized eggs for inter-specific hybridization. This greatly reduces the percentage of real hybrid progenies in the commercial spat batches and also the magnitude of the overall increases in growth of the progenies.

Studies have shown that the hermaphroditic characteristic of the two *Argopecten* scallops is similar to the monoecious characteristic of many agricultural crops. Normally, artificial emasculation is required to solve the problem of same-flower pollination in the breeding of the monoecious crops. Similar situation also exists in the hybridization between the Peruvian scallop and the bay scallop southern subspecies. In agriculture, the key to solve the problem of same-flower pollination depends on the discovery of male sterile (and yet female fertile) plants. A three line breeding system, comprising of the male sterile line, maintainer line and the restorer line can then be obtained by continuously backcrossing the male sterile plant with pollen from an inbreeding line and can be used to produce pure hybrids at commercial scales. So far, the three-line breeding systems have been established in hundreds of agricultural crops around the world and are widely applied in the commercial production of hybrid plants in agriculture.

Up to now, in animal breeding, no male sterile and yet female fertile animals have been found and as a result, no similar three-line breeding system has been established for production of hybrids in animals so far. Obviously, establishment of such three-line breeding systems is essential for the production of inter-specific hybrids between hermaphroditic scallops at large scales and low costs, and represents a major breakthrough in animal breeding technology.

SUMMARY OF THE INVENTION

One object of the present invention is to overcome the deficiency of the existing hybrid scallop breeding technology by establishing a three-line breeding system.

Another object of the present invention is to establish the application method of such three-line breeding system for the efficient production of hybrid seeds from two hermaphroditic scallops, such as the Peruvian scallop and the bay scallop southern subspecies, at large scales and low costs.

The three lines herein refer to the male sterile line, the maintainer line and the restorer line of the scallops. The male sterile line is a line that produces fertilizable eggs, but no functional sperm and is capable of transmitting its male sterile characteristic to its progenies. It is obvious that the male sterile line is the core line in the three line system and plays a key role in providing a large number of unfertilized eggs in commercial production of the hybrid seeds. The reproduction of the male sterile line depends on its corresponding maintainer line. The male sterile line is obtained by continuously backcrossing the accidentally discovered male-sterile but yet female-fertile individuals in the $F_1$ hybrids with the selfing family of their male parents (sperm-providing scallops) to construct backcross families until all the individuals in the backcross families are male sterile and yet female fertile.

A maintainer line is specific for a certain male sterile line; when the maintainer line is hybridized with the male sterile line, the resulted first filial generation will keep the male sterile characteristic; the major function of the maintainer line is to provide sperms necessary for breeding the male sterile line. The maintainer line is selected together with its corresponding male sterile line. In selecting the male sterile line and its maintainer line, the eggs of the male-sterile but yet female-fertile individuals in the $F_1$ hybrids are fertilized with sperm of the selfing family of their male parent (sperm-providing Bay scallop southern subspecies) to construct backcross families. In the following year, the male- and female fertility of the backcross families are tested. The backcross family that is male-sterile and yet female-fertile becomes the male sterile line and the selfing family of the male parent (sperm-providing Bay scallop southern subspecies) becomes the maintainer line specific for this male-sterile line. In this invention, the maintainer line is a hermaphroditic Bay scallop southern subspecies selfing family that is capable of breeding the next-generation maintainer line through self-fertilization.

The restorer line is also known as the restorer line for a male sterile line. The progenies produced from the eggs of the male sterile line and the sperm of the restorer line are hermaphroditic, both female- and male-fertile. Hence, the role of the restorer line is to provide sperm that are used to fertilize eggs from the male sterile line to produce hybrid seeds in commercial operations. The restorer line is a bay scallop southern subspecies line obtained by continuously backcrossing the sperm of bay scallop southern subspecies with the eggs of the male sterile line until all the backcrossed progenies are hermaphrodites. The restorer line is reproduced by self-fertilization.

The present invention is based on the following ideas and facts: 1) The inventors have discovered in their previous studies that the $F_1$ Peruvian scallop×Bay scallop southern subspecies hybrids that produced with the eggs of the Peruvian scallops and the sperm of the Bay scallop southern subspecies contain 2-10% of male sterile individuals in the *A. purpuratus*×*A. i. concentricus* cohort that produce only fertile eggs but not fertile sperm. The eggs from these $F_1$ hybrids can be fertilized by sperm from the Bay scallop southern subspecies and the resulted fertilized eggs can develop normally to produce backcrossed families. Most backcrossed hybrids exhibited excellent production traits in growth rate and temperature tolerance. Compared with the Peruvian scallops produced at the same time and cultured under same conditions, the average whole body weight of the best backcrossed cohorts was more than 100% higher; 2) Studies also showed that 8-10% individuals in the above backcrossed hybrids are still male sterile and yet female fertile. Thus, it is possible to obtain a combination of a male sterile line (serving as the female parent) and a Bay scallop southern subspecies selfing line (serving as the male parent) whose hybridized progenies are still male sterile and female fertile, by continuously backcrossing the eggs from the male sterile line with the sperm of the Bay scallop southern subspecies line for a couple of generations. This Bay scallop southern subspecies line in the above combination is capable of conferring the male sterile characteristic to the progenies of the male sterile line and is thus referred to as the maintainer line for that specific male sterile line; 3) It has been further discovered that about 90% of the backcrossed hybrids produced from the eggs of the male sterile individuals fertilized with the sperm from the Bay scallop southern subspecies were hermaphroditic. Thus it is possible to obtain a combination of a male sterile line (serving as the female parent) and a Bay scallop southern subspecies selfing line (serving as the male parent) whose hybridized progenies are all hermaphrodites that produce both fertile eggs and sperm, by continuously backcrossing the sperm of the Bay scallop southern subspecies line with the eggs from the male sterile line for a couple of generations. This Bay scallop southern subspecies line in the above combination is capable of restoring the male fertility in their progenies with the male sterile line and is thus referred to as the restorer line for that specific male sterile line;4) In commercial operations, the male sterile (and yet female fertile) brood stocks can be produced at large scales by fertilizing the eggs from the male sterile line with sperm from the maintainer line and commercial hybrid seeds with excellent performance can be produced by fertilizing the eggs of the male sterile stocks with the sperm of the corresponding restorer line at large scales and low costs.

The establishment method of the male sterile line, the maintainer line and the restorer line of the Peruvian scallop× bay scallop southern subspecies hybrids of the present invention is as follows:

1) Production of the Male Sterile Individuals in the Peruvian Scallop×Bay Scallop Southern Subspecies Hybrids and Breeding of the Male Parents Thereof:

Large Peruvian scallop and bay scallop southern subspecies brood stocks are conditioned for maturation synchronously. They are then induced to spawn in individual containers at the same time under close observation by routine air exposure and thermal shock as used in the spawning induction of the bay scallops. The eggs of the Peruvian scallops and the bay scallop southern subspecies are collected, if no sperm release is observed and set aside for 20 min when they are checked under a microscope to make sure no fertilized eggs are present. The sperm of the bay scallops are collected by filtering the seawater containing the sperm through a 500-mesh screen (with a diameter of 25 µm) to remove eggs, any. Then, the $F_1$ Peruvian scallop×bay scallop southern subspecies hybrids are produced by mixing the eggs of the Peruvian scallop with an appropriate amount of sperm from the bay scallop southern subspecies. Meanwhile, the eggs of the bay scallop southern subspecies which provides sperm in the above $F_1$ hybrid are fertilized with its own sperm to make a selfing family for this bay scallop southern subspecies. Due to the very low ratio of the male sterile individuals in the $F_1$ hybrids, a large number of $F_1$ hybrid families need to be established in order to find male sterile individuals for breeding the male sterile line as described below.

2) Breeding of the Male Sterile Line and the Maintainer Line:

In the following year, $F_1$ hybrids are conditioned to mature and induced to spawn. Individuals spawn only eggs and the eggs can be fertilized by sperm from bay scallop southern subspecies are considered as male sterile individuals and chosen for further selection of male sterile line. Meanwhile, large individuals from the selfing family of sperm-providing bay scallop southern subspecies of $F_1$ hybrids are also conditioned to mature. Both the selected male sterile scallops and the bay scallop southern subspecies from the selfing family are induced to spawn at the same time. The spawned eggs of the male sterile scallops are fertilized with sperm of the bay scallop southern subspecies selected from the selfing family to construct backcross families. The next generation selfing family of the sperm-providing bay scallop southern subspecies is also produced by fertilizing its own eggs and sperm.

In the subsequent years, male sterile individuals are again selected from the backcross families from previous year and conditioned to ripeness. The eggs from these male sterile individuals are fertilized with sperm from large individuals selected from the bay scallop southern subspecies selfing family which are again reproduced by self-fertilization. Such backcross breeding is carried out continuously until all the backcross progenies are male sterile and yet female fertile. At this point, the backcross progenies become the male sterile line while the bay scallop selfing family becomes the corresponding maintainer line. In commercial practices, the male sterile line brood stocks are reproduced by fertilizing the eggs from the scallops of the male sterile line with the sperm of the bay scallop southern subspecies of the maintainer line, and the maintainer line brood stocks are reproduced by self-fertilization.

3) Breeding of the Restorer Line:

After the male sterile line and its corresponding maintainer line combination is obtained, excellent male sterile individuals from the male sterile line are selected and conditioned to mature. After spawning induction, the eggs from a male sterile individual are fertilized with sperm from different bay scallop southern subspecies to construct backcross families. The eggs from this male sterile individual are mixed with sperm from its corresponding maintainer line to produce the next generation male sterile line. The sperm-providing bay scallop southern subspecies is also reproduced by self-fertilization. During the adult grow-out stage, the growth and survival rates of the hybrid progenies are measured and combining ability tests are carried out.

In the following year, excellent individuals are selected from both the male sterile line and the corresponding sperm-providing Bay scallop southern subspecies selfing family that correlated to the best backcross family with the highest growth and survival rate and highest percentage of hermaphroditic individuals and conditioned to mature. After spawning induction, the eggs from the male sterile individual are again fertilized with sperm of the selected Bay scallop southern subspecies to produce next generation backcross families. Same selection is repeated each year until the backcross families are all hermaphroditic and excellent in production traits. The Bay scallop southern subspecies selfing family that can render male fertility to the progenies of the male sterile line becomes the restorer line. The restorer line can be reproduced by self-fertilization as they are hermaphrodites. In commercial operations, the restorer line is used to provide sperm that can be mixed with eggs from the male sterile line to produce commercial hybrid spats at large scales and low costs.

5) Reproduction of the Male Sterile Line, the Maintainer Line and the Restorer Line:

This invention also establishes the methods for the reproduction of the male sterile line, the maintainer line and the restorer line. The next generation male sterile line is reproduced by fertilizing the eggs from the male sterile line with sperm from its corresponding maintainer line. The next generation maintainer line and the restorer line are reproduced by self-fertilization, i.e., fertilization of eggs with their own sperm, as both lines are hermaphroditic Bay scallop southern subspecies.

6) Production of Commercial Hybrid Spats Using the Three-Line Breeding System:

The brood stocks of the male sterile line and the restorer line are selected in the ratio of 5:1. After the scallops are conditioned to ripeness using the conventional methods, the brood stocks of the male sterile are induced to spawn eggs and the scallops of the restorer line are induced to spawn eggs and sperm. Then seawater containing the sperm-eggs mixture of the restorer line is filtered using a 500-mesh screen (with a diameter of 25 μm) to collect sperm of the restorer line, which is added to the spawning tank of the male sterile line and stirred. Seawater samples from the spawning tanks are frequently checked under a microscope until each egg is surrounded by 5-6 sperm. Commercial hybrid spats are obtained after the fertilized eggs hatch.

The present invention can be used in the construction and application of similar three-line breeding system between all hermaphroditic *Argopecten* scallops including, but not limited to *Argopecten irradians irradians, A. irradians concentricus, A. purpuratus, A. gibbus*, and *A. ventricosus*, etc. Furthermore, the methods outlined in this invention can also be used in other hermaphroditic scallops such as the *Pecten* scallops and even in other hermaphroditic invertebrates.

The three-line breeding system of the Peruvian scallop× bay scallop southern subspecies hybrids established in this invention is the first three-line breeding system established in the scallops and also in the animal kingdom, representing a major breakthrough in the animal breeding technology. The present invention effectively overcomes the barrier of self-fertilization in the hybridization process of the hermaphroditic scallops and enables complete hybridization at large scales and low costs. Therefore, the hybrid vigor can be fully utilized in the hybrid progenies which possess the advantages of both scallops in terms of growth, body size and temperature tolerance, etc. Hence, the Peruvian scallop× bay scallop southern subspecies hybrids can be successfully cultured in southern China seas such as Fujian and Guangxi Province, with an increase in yield by over 50% in the first year compared with the bay scallops.

DETAILED DESCRIPTION OF THE EMBODIMENTS

The present invention establishes a three-line breeding system, comprising of a male sterile line, a maintainer line and a restorer line of Peruvian scallop×bay scallop southern subspecies hybrids and also application methods for commercial production of the Peruvian scallop×bay scallop southern subspecies hybrid spats using the three-line breeding system. The specific steps are as follows:

Embodiment 1

1) Production of the Male Sterile Individuals of the Peruvian Scallop×Bay Scallop Southern Subspecies Hybrids and Reproduction of the Sperm-Providing Bay Scallop Southern Subspecies:

In the first year, 50 Peruvian scallops and 50 bay scallop southern subspecies with mature gonads are selected. After air exposure for 30 min., scallops are placed in separate containers, pre-filled with 23° C. seawater for spawning induction. After spawning, the eggs and sperm of each scallop are collected separately. Eggs of a Peruvian scallop are mixed with sperm of a bay scallop southern subspecies to produce a Peruvian scallop×bay scallop southern subspecies $F_1$ hybrid family. A selfing family is produced for each sperm-providing bay scallop southern subspecies by mixing its eggs with its own sperm. In all cases, only a small amount of sperm are used to avoid adverse effect caused by excess sperm. Ideally, each egg should be surrounded by 5-6 sperm. The fertilized eggs are hatched in dark and the resulted D-larvae are collected. At least 20 $F_1$ hybrid families and the corresponding selfing family of the sperm-providing bay scallop southern subspecies are established. Larval culture, spat nursery and adult grow-out are carried out following the routine culture methods for the Peruvian scallops.

2) Breeding of the Male Sterile Line of the Peruvian Scallop×Bay Scallop Southern Subspecies Hybrids:

In the next spring, at least 100 individuals with excellent production traits and apparent male sterile gonad (with no obvious gonadal development in the male part of the gonad) are selected from each $F_1$ hybrid family. Twenty scallops with excellent production traits are also selected from each selfing families of the corresponding sperm-providing bay scallop southern subspecies. After conditioning, test spawning is carried out to determine if the individuals selected from the $F_1$ hybrid families spawn only eggs and the eggs can be fertilized and thus to select the male sterile and yet female fertile F$_1$ hybrid families. Then at least 50 backcross families are constructed with the eggs from selected male sterile/female fertile individuals and sperm from selected individuals from the corresponding selfing families of the sperm-providing bay scallop southern subspecies. The sperm-providing bay scallop southern subspecies brood stocks of the backcross families are again reproduced by self-fertilization. In the following years, the male sterile/female fertile individuals from the backcross families are continuously backcrossed with individuals selected from the selfing family of the sperm-providing bay scallop southern subspecies, until all the individuals of the backcross progenies exhibit excellent traits and are male sterile and female fertile. The male sterile line of the Peruvian scallop×bay scallop southern subspecies hybrids is thus obtained and the selfing family of the sperm-providing bay scallop southern subspecies becomes the corresponding maintainer line for this male sterile line.

3) Breeding of the Maintainer Line of the Peruvian Scallop× Bay Scallop Southern Subspecies Hybrids:

Individuals with excellent production traits are selected from the maintainer line and conditioned to mature. As the scallops of the maintainer line are hermaphroditic animals, the maintainer line is reproduced by self-fertilization.

4) Breeding of the Restorer Line of the Peruvian Scallop× Bay Scallop Southern Subspecies Hybrids:

Fifty large male sterile and female fertile individuals are selected from the male sterile line and the maintainer line respectively and conditioned to ripeness. They are then induced to spawn and the eggs from the male sterile individuals are fertilized by the sperm of different bay scallop southern subspecies to establish at least 20 backcross families; meanwhile, the sperm-providing bay scallop southern subspecies are self-fertilized to establish the corresponding self-fertilization families. At harvest, the growth and survival rates of the backcross progenies are measured and the combining ability tests are carried out for each backcross family. In the following year, excellent individuals are selected from both the male sterile line and the corresponding sperm-providing bay scallop southern subspecies selfing family that correlated to the best backcross family with the highest combining ability and highest percentage of hermaphroditic individuals. After conditioning and spawning induction, eggs from the male sterile line are again backcrossed with the sperm of the selected individual from the selfing family of the sperm-providing bay scallop. Same selections are carried each year on the selfing family of the sperm-providing bay scallop southern subspecies until all individuals in the backcross family are hermaphroditic and exhibit excellent production traits. This selfing family of the sperm-providing bay scallop becomes the restorer line for the corresponding male sterile line. The hermaphroditic restorer line is reproduced by self-fertilization and provides sperm for the commercial production of hybrid spats.

5) Production of Commercial Peruvian Scallop×Bay Scallop Southern Subspecies Hybrid Spats Using the Three-Line Breeding System:

Each year, the brood stocks of the male sterile line are produced by hybridizing the male sterile line with the sperm of its maintainer line while the brood stocks of the restorer line are reproduced by self-fertilization. In commercial scallop hatcheries, the brood stocks of the male sterile line and the restorer line are selected in the ratio of 5:1 and conditioned to ripeness at the same time. Then the brood stocks of the male sterile line are induced to spawn in large tanks and the brood stocks of the restorer line are induced to spawn in 20 liter buckets. The sperm of the restorer line are collected by filtering the seawater in the buckets through a 500-mesh screen and added to the spawning tanks containing the eggs from the male sterile line brood stocks and well stirred immediately. Seawater samples are taken frequently from the tanks for observation of the fertilization under a microscope until 5-6 sperm are found around each egg. The commercial Peruvian scallop-bay scallop southern subspecies hybrid seeds can thus be produced at large scales and low costs.

Embodiment 2

In 2012, large individuals with only female part of gonads developed were selected from the F$_1$ Peruvian scallop×bay scallop southern subspecies (*A. i. concentricus*) hybrid family constructed in 2011 using the bay scallop southern subspecies from Zhanjing, Guangdong Province of China. After conditioning and spawning induction, two backcross families were constructed with the spawned eggs fertilized with sperm from a Bay scallop southern subspecies. At harvest in mid-November 2012, the average shell height, average shell length, average shell width and the average whole weight of the backcross families were increased by 28.5-29.7%, 28.3-29.6%, 18.5-19.1% and 91.2-93.2%, respectively. The results showed that the backcross family exhibited great production traits in growth.

After maturation in the spring of 2013, it was discovered that the progenies of the (Peruvian scallop×bay scallop southern subspecies)×bay scallop southern subspecies backcross families were all hermaphrodites, indicating that the restorer line of the male sterile line can be successfully bred by backcrossing the bay scallop southern subspecies with the male sterile individuals. In most progenies in another (Peruvian scallop×bay scallop southern subspecies)×bay scallop southern subspecies family, only the female part of their gonads developed and furthermore, the spawned eggs can be fertilized by bay scallop southern subspecies sperm, suggesting that it is possible to breed the male sterile line and the maintainer line by continuously backcrossing the Bay scallop southern subspecies with the male sterile individuals.

Embodiment 3

In 2013 and 2014, 14 F$_1$ Peruvian scallop×bay scallop southern subspecies (*A. i. concentricus*) hybrid families together with the selfing families of their sperm-providing bay scallop southern subspecies were established. According to the methods given in Embodiment 1, the male sterile families of the Peruvian scallop-bay scallop southern subspecies hybrids and the corresponding maintainer line and restorer line thereof can be bred and the production of commercial Peruvian scallop-bay scallop southern subspecies hybrid spats can be realized within 1-3 years.

The invention claimed is:

1. A three-line breeding, system using Peruvian scallop× Bay scallop southern subspecies hybrids, the system comprising:
    a male sterile line, comprising a Peruvian scallop×Bay scallop southern subspecies hybrid line that is male-sterile and yet female-fertile and spawns only eggs;
    a maintainer line, comprising a Bay scallop southern subspecies line that provides sperm to fertilize eggs of the male-sterile line to produce a next generation male-sterile line; and a restorer line, comprising a Bay scallop southern subspecies line that provides sperm to fertilize eggs of the male-sterile line to produce commercial hermaphroditic hybrid scallops.

2. A three-line breeding method using Peruvian scallop×Bay scallop southern subspecies hybrids, the method comprising:
1) selecting $F_1$ male-sterile individuals from $F_1$ Peruvian scallop×Bay scallop southern subspecies hybrid families and also Bay scallop southern subspecies individuals from the corresponding selfing Bay scallop southern subspecies family, comprising:
1a) producing, for step 1b, $F_1$ hybrid families wherein each family is produced using eggs from a Peruvian scallop and sperm from a Bay scallop southern subspecies, meanwhile each Bay scallop southern subspecies that provides sperm is used to produce a corresponding selfing Bay scallop southern subspecies family for step 1c;
1b) selecting, for step 2a, male-sterile individuals from the $F_1$ hybrid families produced in step 1a, wherein the individual is determined to be male-sterile if it only spawns eggs; and
1c) selecting, for step 2a, Bay scallop southern subspecies individuals from each corresponding selfing Bay scallop southern subspecies family produced in step 1a;
2) breeding a male-sterile line, comprising:
2a) Producing, for step 2b, backcross families wherein each backcross family is produced using eggs from a selected male-sterile $F_1$ hybrid individual produced in step 1b and sperm from the corresponding selected Bay scallop southern subspecies individual selected in step 1c, meanwhile each Bay scallop southern subspecies that provides sperm is used to produce a corresponding selfing Bay scallop southern subspecies family for step 2b and step 2d;
2b) selecting from the backcross families produced in step 2a, for step 2c, a backcross family wherein each individual in this family is male-sterile/female-fertile, wherein the individual is determined to be male-sterile/female-fertile if it spawns only eggs and the spawned eggs can be fertilized by sperm of the selected Bay scallop southern subspecies individuals from the corresponding selfing Bay scallop southern subspecies family produced in step 2a and produce progenies;
2c) obtaining a male-sterile line, wherein the backcross family produced in step 2b is selected as the male-sterile line; and
2d) selecting, for step 3, the selfing Bay scallop southern subspecies family corresponding to the male-sterile line selected in step 2c;
3) obtaining a maintainer line from step 2d, wherein the selfing Bay scallop southern subspecies family selected in step 2d is selected as the maintainer line specific for the male-sterile line produced in step 2c, as this selfing Bay scallop southern subspecies family is able to render the male-sterile/female-fertile characteristics to the progenies of the male-sterile line produced in step 2c;
4) breeding a restorer line, comprising:
4a) producing, for step 4b, hybrid families using eggs from individuals of the male-sterile line produced in step 2c and sperm of Bay scallop southern subspecies that are not genetically related to the male-sterile line produced in step 2c, meanwhile each Bay scallop southern subspecies that provides sperm is used to produce a corresponding selfing family for step 4c;
4b) selecting, from the hybrid families produced in step 4a, a hybrid family wherein each individual in this hybrid family is hermaphroditic; and
4c) selecting a restorer line, which is the selfing Bay scallop southern subspecies family produced in step 4a corresponding to the hybrid family selected in step 4b, as this selfing Bay scallop southern subspecies family is able to restore the male-fertility of the progenies of the male sterile line produced in step 2c; and
5) reproducing the three-line breeding system, wherein a next generation of male-sterile line is produced by fertilizing the eggs of the male-sterile line produced in step 2c with the sperm from the corresponding maintainer line produced in step 3, and the commercial hermaphroditic hybrid scallops are produced by fertilizing the eggs of the male-sterile line produced in step 2c with the sperm from the corresponding restorer line produced in step 4c.

* * * * *